United States Patent
Sakamoto et al.

(10) Patent No.: US 11,090,014 B2
(45) Date of Patent: Aug. 17, 2021

(54) DENTAL IMAGE PROCESSING DEVICE, DENTAL IMAGING SYSTEM, DENTAL IMAGE PROCESSING METHOD, AND PROGRAM

(71) Applicant: NIIGATA UNIVERSITY, Niigata (JP)

(72) Inventors: Makoto Sakamoto, Niigata (JP); Koichi Kobayashi, Niigata (JP); Yusuke Morise, Niigata (JP); Yuta Sakagami, Niigata (JP); Takashi Kameda, Tokyo (JP)

(73) Assignee: NIIGATA UNIVERSITY, Niigata (JP)

( * ) Notice: Subject to any disclaimer, the term of this patent is extended or adjusted under 35 U.S.C. 154(b) by 8 days.

(21) Appl. No.: 16/756,446

(22) PCT Filed: Oct. 22, 2018

(86) PCT No.: PCT/JP2018/039182
§ 371 (c)(1),
(2) Date: Apr. 15, 2020

(87) PCT Pub. No.: WO2019/082841
PCT Pub. Date: May 2, 2019

(65) Prior Publication Data
US 2021/0196213 A1 Jul. 1, 2021

(30) Foreign Application Priority Data
Oct. 23, 2017 (JP) .............................. JP2017-204342

(51) Int. Cl.
*A61B 6/14* (2006.01)
*A61B 6/00* (2006.01)
*A61B 6/03* (2006.01)

(52) U.S. Cl.
CPC ................ *A61B 6/14* (2013.01); *A61B 6/032* (2013.01); *A61B 6/466* (2013.01)

(58) Field of Classification Search
CPC ............ A61B 6/14; A61B 6/466; A61B 6/032
See application file for complete search history.

(56) References Cited

FOREIGN PATENT DOCUMENTS

| JP | 8-131403 A | 5/1996 |
|---|---|---|
| JP | 2017-520292 A | 7/2017 |
| WO | WO 01/003065 A1 | 1/2001 |

OTHER PUBLICATIONS

PCT International Search Report and Written Opinion, International Application No. PCT/JP2018/039182, dated Nov. 27, 2018, 8 Pages.

(Continued)

*Primary Examiner* — Courtney D Thomas
(74) *Attorney, Agent, or Firm* — Fenwick & West LLP

(57) ABSTRACT

In an image processing device (300), a position determiner (313) determines, in a three-dimensional image showing an upper jaw part of a subject and a lower jaw part of the subject, positions of left and right mental foramina of the lower jaw part and a position of an incisors tube of the upper jaw part. A coordinate system setter (314) sets a three-dimensional coordinate system having an origin at a position established by the positions of the left and right mental foramina and the position of the incisors tube that are determined by the position determiner (313), the three-dimensional coordinate system including: a first coordinate axis that passes through the origin and the position of the incisors tube; a second coordinate axis that is perpendicular to the first coordinate axis and a straight line connecting the position of the left mental foramen and the position of the right mental foramen; and a third coordinate axis that is perpendicular to the first coordinate axis and the second coordinate axis.

14 Claims, 8 Drawing Sheets

(56) References Cited

OTHER PUBLICATIONS

Kim, G., et al., "Automatic Teeth Axes Calculation for Well-Aligned Teeth Using Cost Profile Analysis Along Teeth Center Arch," IEEE Transactions on Biomedical Engineering, Apr. 2012, vol. 59, No. 4, pp. 1145-4454.

Sakamoto, M., et al., "A novel method for three-dimensional anterior tooth axis and alignment using in vivo cone-beam computed tomographic image," $8^{th}$ World Congress of Biomechanics, Jul. 9, 2018, Dublin, Ireland.

Sakamoto, M., et al., "Evaluation of the three-dimensional tooth axis using micro-CT," Japanese Society of Clinical Biomechanics, 2014, vol. 35, pp. 99-104. (with English Abstract).

Sakamoto, M., et al., "Automatic three-dimensional tooth axis using cone beam CT," Materials Science, 2015, vol. 36, pp. 119-125. (with English Abstract).

Shiingo, I., et al., "A Study on the Tooth-axis about Upper Central Incisors," Journal of Japan Prosthodontic Society, 2004, vol. 48, pp. 74-83. (with English Abstract).

and a program therefor that can suitably evaluate a relative relationship between a plurality of teeth.

Solution to Problem

In order to attain the above objective, a dental image processing device according to a first aspect of the present disclosure includes:

position determination means for determining, in a three-dimensional image showing an upper jaw part of a subject and a lower jaw part of the subject, a position of a left mental foramen of the lower jaw part, a position of a right mental foramen of the lower jaw part, and a position of an incisors tube of the upper jaw part; and coordinate system setting means for setting a three-dimensional coordinate system having an origin at a position established by the position of the left mental foramen, the position of the right mental foramen, and the position of the incisors tube that are determined by the position determination means, the three-dimensional coordinate system including: a first coordinate axis that passes through the origin and the position of the incisors tube; a second coordinate axis that is perpendicular to the first coordinate axis and a straight line connecting the position of the left mental foramen and the position of the right mental foramen; and a third coordinate axis that is perpendicular to the first coordinate axis and the second coordinate axis.

The coordinate system setting means may define, as the origin, a position that internally divides, by a specified ratio, a distance from a middle point of the position of the left mental foramen and the position of the right mental foramen determined by the position determination means, to the position of the incisors tube determined by the position determination means.

The coordinate system setting means may define:

as a temporary coordinate axis, a vector from the position of the left mental foramen to the position of the right mental foramen;

as the first coordinate axis, a vector passing through the position of the incisors tube from the middle point;

the second coordinate axis by a cross product of the first coordinate axis and the temporary coordinate axis; and the third coordinate axis by a cross product of the second coordinate axis and the first coordinate axis.

The dental image processing device may further include:

information acquisition means for acquiring information on a tooth of at least one of the upper jaw part or the lower jaw part, the information being represented by the three-dimensional coordinate system set by the coordinate system setting means; and output means for outputting the information on the tooth acquired by the information acquisition means.

The information acquisition means may acquire, as the information on the tooth, position coordinates of a plurality of teeth of at least one of the upper jaw part or the lower jaw part.

The information acquisition means may acquire a position coordinate of a center of gravity of each of the plurality of teeth.

The information acquisition means may acquire an approximate curve for approximating the position coordinates of the plurality of teeth, and the output means may output the position coordinates of the plurality of teeth and the approximate curve acquired by the information acquisition means.

DENTAL IMAGE PROCESSING DEVICE, DENTAL IMAGING SYSTEM, DENTAL IMAGE PROCESSING METHOD, AND PROGRAM

TECHNICAL FIELD

The present disclosure relates to a dental image processing device, a dental imaging system, a dental image processing method, and a program therefor.

BACKGROUND ART

A technique has been known to determine a tooth axis as an index representing the characteristics of a tooth. For example, Non Patent Literature 1 discloses a technique to measure in vitro, a surface shape of a maxillary central incisor by way of a noncontact laser measuring instrument and determine a tooth axis by using the principle component analysis method. In addition, Non Patent Literature 2 discloses a technique to acquire an in vivo CT image of 20 human teeth by using a dental cone-beam computed tomography (CBCT) and determine a tooth axis by using the principle component analysis method. Further, Non Patent Literature 3 and Non Patent Literature 4 disclose a technique to manually separate a dental root part from a jawbone from a CT image of a tooth to construct a three-dimensional shape of the tooth and determine a three-dimensional tooth axis by using the principle component analysis method.

CITATION LIST

Non Patent Literature

Non Patent Literature 1: Iijima Shingo, Kasahara Shin, Kimura Kohei, Kikuchi Masayoshi & Muramoto Mutsushi, "A study on the teeth-axis about upper central incisors—Determination of quantitative tooth axis—", J Jpn Prosthodont Soc 48, pp. 74-83, 2004

Non Patent Literature 2: G. Kim, et al., "Automatic teeth axes calculation for well-aligned teeth using cost profile analysis along teeth center arch", IEEE Trans Biomed Eng, Vol. 59, No. 4, pp. 1145-1154, April 2012

Non Patent Literature 3: Makoto SAKAMOTO, Yuto KASUGA, Sachiko HAYASHI-SAKAI, Koichi KOBAYASHI & Hideaki ENDO, "Evaluation of the three-dimensional tooth axis using micro-CT", Japanese Journal of Clinical Biomechanics, Vol. 35, pp. 99-104, 2014

Non Patent Literature 4: Makoto SAKAMOTO, Yuto KASUGA, Sachiko HAYASHI-SAKAI, Koichi KOBAYASHI & Hideaki ENDO, "Automatic three-dimensional tooth axis using cone beam CT", Japanese Journal of Clinical Biomechanics, Vol. 36, pp. 119-125, 2015

SUMMARY OF INVENTION

Technical Problem

Still, the techniques disclosed in Non Patent Literature 1 to Non Patent Literature 4 determine a tooth axis in a local coordinate system set for each individual tooth. This presents a problem that it is difficult to evaluate a relative relationship between a plurality of teeth.

The present disclosure has been made in consideration of the above circumstances and has an objective to provide a dental image processing device, a dental imaging system, a The information acquisition means may acquire, as the approximate curve, a curve obtained by regressing the position coordinates of the plurality of teeth by using a quadratic function.

The output means may output information indicating a difference between each of the position coordinates of the plurality of teeth acquired by the information acquisition means and the approximate curve acquired by the information acquisition means.

The output means may display an image representing each of the plurality of teeth at a position distant, by a magnitude of the difference in a direction of the difference, from each of the position coordinates of the plurality of teeth acquired by the information acquisition means in the three-dimensional coordinate system set by the coordinate system setting means.

The information acquisition means may acquire, as the information on the tooth, a tooth axis of the tooth.

In order to attain the above objective, a dental imaging system according to a second aspect of the present disclosure includes:

the dental image processing device; and image capturing means for capturing images of the upper jaw part and the lower jaw part of the subject, wherein the position determination means determines, in the three-dimensional image obtained via capturing by the image capturing means, the position of the left mental foramen, the position of the right mental foramen, and the position of the incisors tube.

In order to attain the above objective, a dental image processing method according to a third aspect of the present disclosure includes:

determining, in a three-dimensional image showing an upper jaw part of a subject and a lower jaw part of the subject, a position of a left mental foramen of the lower jaw part, a position of a right mental foramen of the lower jaw part, and a position of an incisors tube of the upper jaw part; and setting a three-dimensional coordinate system having an origin at a position established by the determined position of the left mental foramen, the determined position of the right mental foramen, and the determined position of the incisors tube, the three-dimensional coordinate system including: a first coordinate axis that passes through the origin and the position of the incisors tube; a second coordinate axis that is perpendicular to the first coordinate axis and a straight line connecting the position of the left mental foramen and the position of the right mental foramen; and a third coordinate axis that is perpendicular to the first coordinate axis and the second coordinate axis.

In order to attain the above objective, a program according to a fourth aspect of the present disclosure causes a computer to function as:

position determination means for determining, in a three-dimensional image showing an upper jaw part of a subject and a lower jaw part of the subject, a position of a left mental foramen of the lower jaw part, a position of a right mental foramen of the lower jaw part, and a position of an incisors tube of the upper jaw part; and coordinate system setting means for setting a three-dimensional coordinate system having an origin at a position established by the position of the left mental foramen, the position of the right mental foramen, and the position of the incisors tube that are determined by the position determination means, the three-dimensional coordinate system including: a first coordinate axis that passes through the origin and the position of the incisors tube; a second coordinate axis that is perpendicular to the first coordinate axis and a straight line connecting the position of the left mental foramen and the position of the right mental foramen; and a third coordinate axis that is perpendicular to the first coordinate axis and the second coordinate axis.

Advantageous Effects of Invention

According to the present disclosure, it is possible to suitably evaluate a relative relationship of a plurality of teeth.

DESCRIPTION OF EMBODIMENTS

Figure 1:
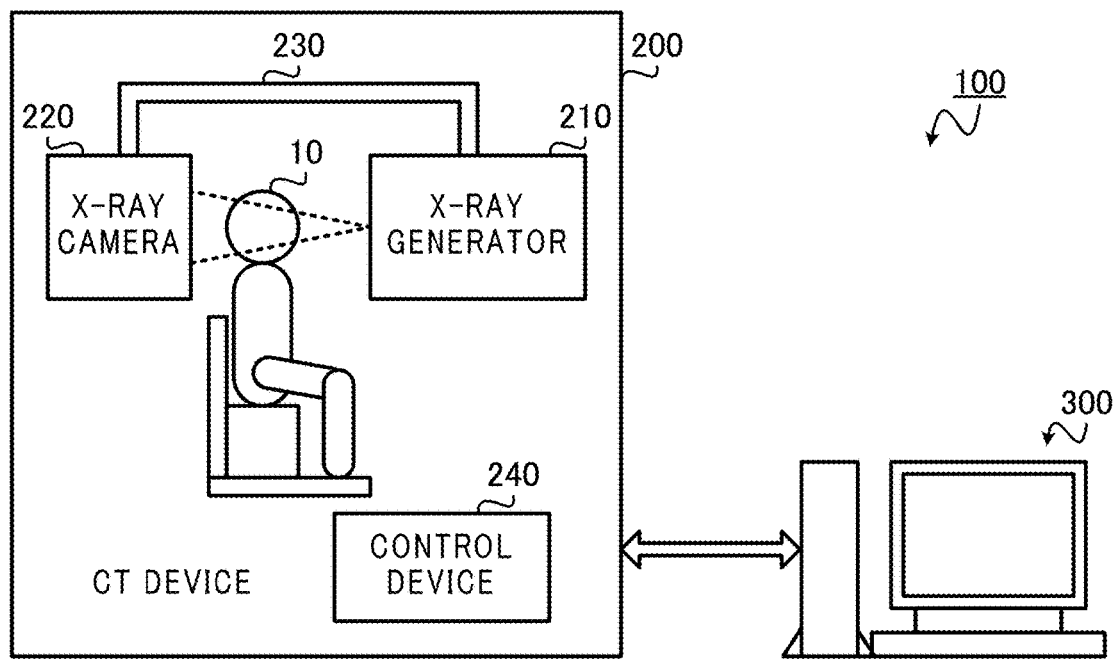
FIG. 1 shows an overall configuration of an imaging system according to an embodiment of the present disclosure.

Embodiments of the present disclosure will be described referring to drawings. Note that the same or corresponding parts are given the same reference numerals in the figures.

FIG. 1 shows an overall configuration of an imaging system 100 according to an embodiment of the present disclosure. The imaging system 100 is a dental system that has an objective to image and diagnose a tooth of a subject 10. As shown in FIG. 1, the imaging system 100 includes a CT device 200 and an image processing device 300. The CT device 200 and the image processing device 300 are communicatively coupled to each other via a wired or wireless communication network.

The CT device 200 is an imaging device for acquiring a three-dimensional image of the subject 10 and is in particular a dental computer tomographic imaging device for acquiring a tomographic image (CT image) of a region, as a target of imaging, including a tooth of the subject 10, by way of the cone beam system. The subject 10 is a target person of an examination and is, as an example, a patient that receives a medical care at a medical facility such as a dental clinic or an oral surgery clinic. The CT device 200 is installed in an examination room of such a medical facility.

The CT device 200 functions as image capturing means for imaging a region including an upper jaw part and a lower jaw part of the subject 10 as an imaging region (target of imaging). In particular, as shown in FIG. 1, the CT device 200 includes an X-ray generator 210, an X-ray camera 220, an arm 230, and a control device 240.

The X-ray generator 210 generates an X-ray in response to an instruction from the control device 240. In particular, the subject 10 has his/her head fixed by a fixer (not shown) while being seated in a chair in the CT device 200. When an operator manipulates a switch to start imaging in this state, the control device 240 causes the X-ray generator 210 to generate an X-ray. The X-ray generated by the X-ray generator 210 has its irradiation range (for example, a range shown by dotted lines in FIG. 1) narrowed by a diaphragm and is irradiated toward an imaging region of the subject 10. The X-ray irradiated from the X-ray generator 210 onto the subject 10 is detected by the X-ray camera 220.

The X-ray camera 220 includes an image sensor such as a charge coupled device (CCD) or a complementary metal-oxide-semiconductor (CMOS) that is X-ray sensitive, and detects, via the image sensor, the X-ray generated by the X-ray generator 210. This acquires a CT image obtained by X-ray imaging of the imaging region of the subject 10.

The X-ray generator 210 and the X-ray camera 220 are held by the arm 230 while being opposed to each other across the subject 10. The arm 230 rotates in response to an instruction by the control device 240. This causes the X-ray generator 210 and the X-ray camera 220 to move around the subject 10 while being opposed to each other. It is thus possible to image the imaging region of the subject 10 from various directions.

The control device 240 includes a processor such as a central processing unit (CPU), a memory such as a read-only memory (ROM), a random access memory (RAM) or a flash memory, a user interface, and a communication interface. The control device 240 controls the operation of an entirety of the CT device 200 and causes the CT device 200 to operate as described above in accordance with an instruction from the operator. This obtains a plurality of CT images created by X-ray imaging of the imaging region including the upper jaw part and the lower jaw part of the subject 10 from various directions.

Figure 2:
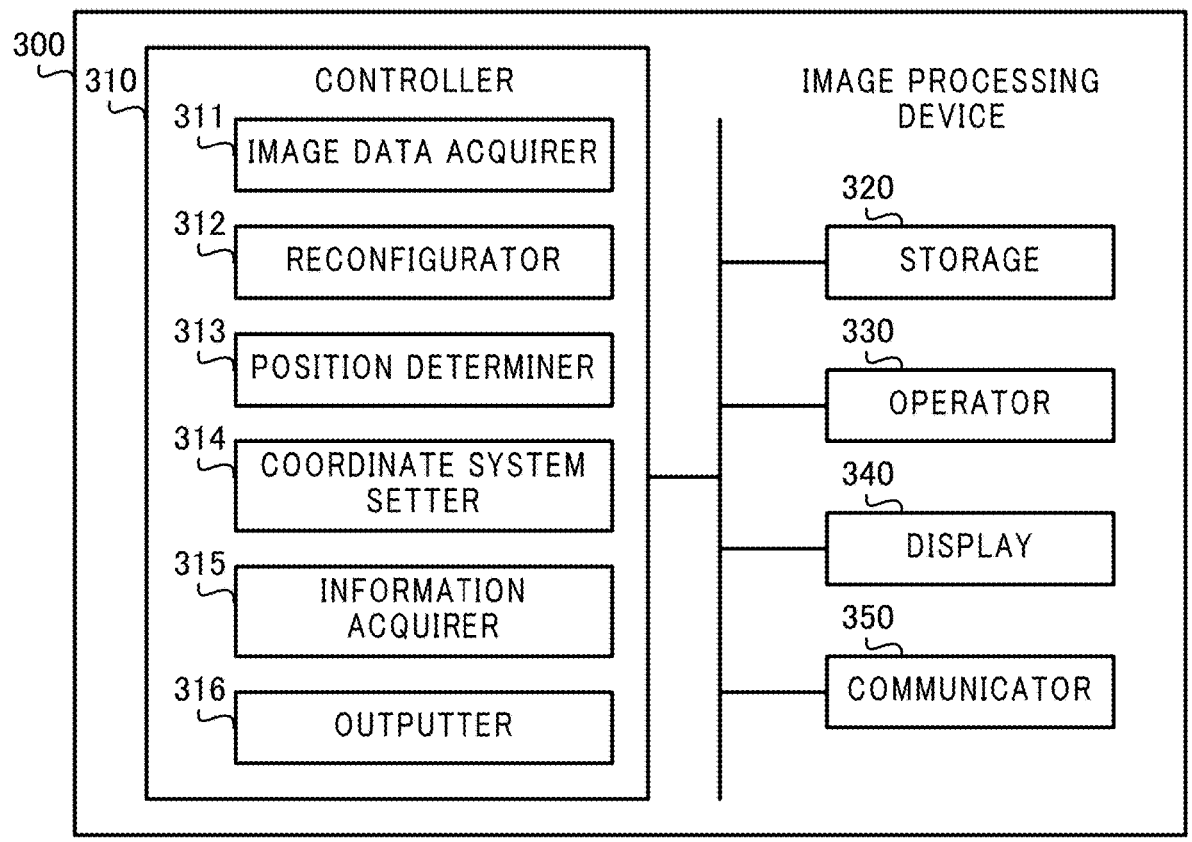
FIG. 2 is a block diagram showing a configuration of an image processing device according to the embodiment of the present disclosure.

The image processing device 300 is a terminal device operated by an operator, such as a personal computer or a tablet terminal. As an example, the image processing device 300 is installed inside a medical facility where the CT device 200 is installed. As shown in FIG. 2, the image processing device 300 includes a controller 310, a storage 320, an operator 330, a display 340, and a communicator 350. These components are interconnected via a bus for transmitting signals.

The controller 310 includes a CPU, a ROM and a RAM. The CPU, which may be a microprocessor or the like, is a central processing unit for performing various types of processing and operations. In the controller 310, the CPU reads a control program stored in the ROM and controls the operation of an entirety of the image processing device 300 while using the RAM as a work memory.

The storage 320 is a nonvolatile memory such as a flash memory or a hard disk. The storage 320 stores a program and data, which include an operating system (OS) and an application program, used by the controller 310 to perform various types of processing. The storage 320 stores data generated or obtained by various types of processing performed by the controller 310.

The operator 330 includes an input device such as a keyboard, a mouse, a button, a touch pad, or a touch panel and receives an operation from an operator. The operator can input a command directed to the image processing device 300 by manipulating the operation device 330.

The display 340 includes a display portion such as a liquid-crystal display or an organic electro luminescence (EL) display, and a display drive circuit for displaying an image on the display portion. The display 340 displays a CT image acquired from the CT device 200 and a three-dimensional image of the subject 10 reconfigured from the CT image. In this way, the display 340 displays various types of information obtained as a result of processing by the controller 310.

The communicator 350 is an interface for communicating with an external device including a CT device 200. The image processing device 300 is connected to the CT device 200 via a communication line conforming to a wired local area network (LAN), a wireless LAN, or any other communication standard. The communicator 350 communicates with the CT device 200 under the control by the controller 310 and acquires CT image data from the CT device 200. The communicator 350 can be connected to a wide area network such as the Internet via wired or wireless communications.

As shown in FIG. 2, the controller 310 functionally includes an image data acquirer 311, a reconfigurator 312, a position determiner 313, a coordinate system setter 314, an information acquirer 315, and an outputter 316. In the controller 310, the CPU reads a program stored in the ROM into the RAM and executes the program for control practices, which causes each of these components to function individually.

The image data acquirer 311 acquires image data obtained through CT imaging of the subject 10 via the CT device 200. In particular, the image data acquirer 311 communicates with the CT device 200 via the communicator 350 and acquires image data indicating a plurality of CT images obtained by CT imaging of the subject 10 from various directions from the CT device 200. The image data thus obtained is stored in the storage 320. The image data acquirer 311 works through coordination of the controller 310 with the communicator 350. The image data acquirer 311 functions as image data acquisition means.

The reconfigurator 312 reconfigures or reconstructs a three-dimensional image based on image data acquired by the image data acquirer 311. The image data acquired by the image data acquirer 311 indicates a plurality of CT images obtained by imaging of an imaging region including the upper jaw part and the lower jaw part of the subject 10 from various directions in the CT device 200. The reconfigurator 312 three-dimensionally reconfigures a plurality of CT images that are each two-dimensional tomographic images, by using a known three-dimensionalization technique. In particular, three-dimensional voxel data is generated from pixel data of a plurality of CT images to generate a three-dimensional image 50 shown, for example, in FIGS. 3 to 7. The reconfigurator 312 works through coordination of the controller 310 with the storage 320. The reconfigurator 312 functions as reconfiguration means.

As shown in FIGS. 3 to 7, the three-dimensional image 50 generated by the reconfigurator 312 shows the upper jaw part and the lower jaw part of the subject 10 as the imaging region by the CT device 200. The upper jaw part is a region including maxillary teeth and bones and the lower jaw part is a region including mandibular teeth and bones. The three-dimensional image 50 generated by the reconfigurator 312 is displayed, as required, on the display 340 and used for diagnosis of the subject 10.

The position determiner 313 determines, in the three-dimensional image 50 generated by the reconfigurator 312, the position of the left mental foramen of the lower jaw part, the position of the right mental foramen of the lower jaw part, and the position of the incisors tube of the upper jaw part (maxillary incisors tube). The mental foramen refers to one of holes existing as a left-right pair in a front face of a mandible. The mental foramen is, typically in an adult, positioned in the middle of a mandibular height below a second premolar or below a point between a first and a second premolar, and a mental nerve, a mental artery and a mental vein pass therein. The maxillary incisors tube is a tube connecting a nasal cavity and an oral cavity and penetrates a maxillary palatine process in an anteroinferior direction from an upper surface to a lower surface. The entrance of the maxillary incisors tube is positioned at a central front part of the rear side of the upper jaw part (palate) and a sphenopalatine artery and a nasopalatine nerve pass in the maxillary incisors tube.

The positions of the left and right mental foramina and the position of the maxillary incisors tube are used, by the coordinate system setter 314, as reference positions for setting a world coordinate system. The operator manually identifies the positions of the left and right mental foramina and the position of the maxillary incisors tube of the subject 10 while watching the three-dimensional image 50 displayed on the display 340, and manipulates the operator 330 to input the identified positions to the image processing device 300. The position determiner 313 determines the positions thus input by the operator via the operator 330 as the positions of the left and right mental foramina and the position of the maxillary incisors tube. The position determiner 313 works through coordination of the controller 310 with the operator 330 and the display 340. The position determiner 313 functions as position determination means.

The coordinate system setter 314 sets a world coordinate system based on the position of the left mental foramen, the position of the right mental foramen and the position of the incisors tube determined by the position determiner 313. A world coordinate system, also called a global coordinate system, is a three-dimensional coordinate system representing an entirety of the three-dimensional image 50. In contrast to a local coordinate system individually set for each tooth, a world coordinate system is a coordinate system used to comprehensively evaluate an entirety of a plurality of teeth included in the three-dimensional image 50. A procedure for setting a world coordinate system will be described referring to FIGS. 3 to 7.

Figure 3:
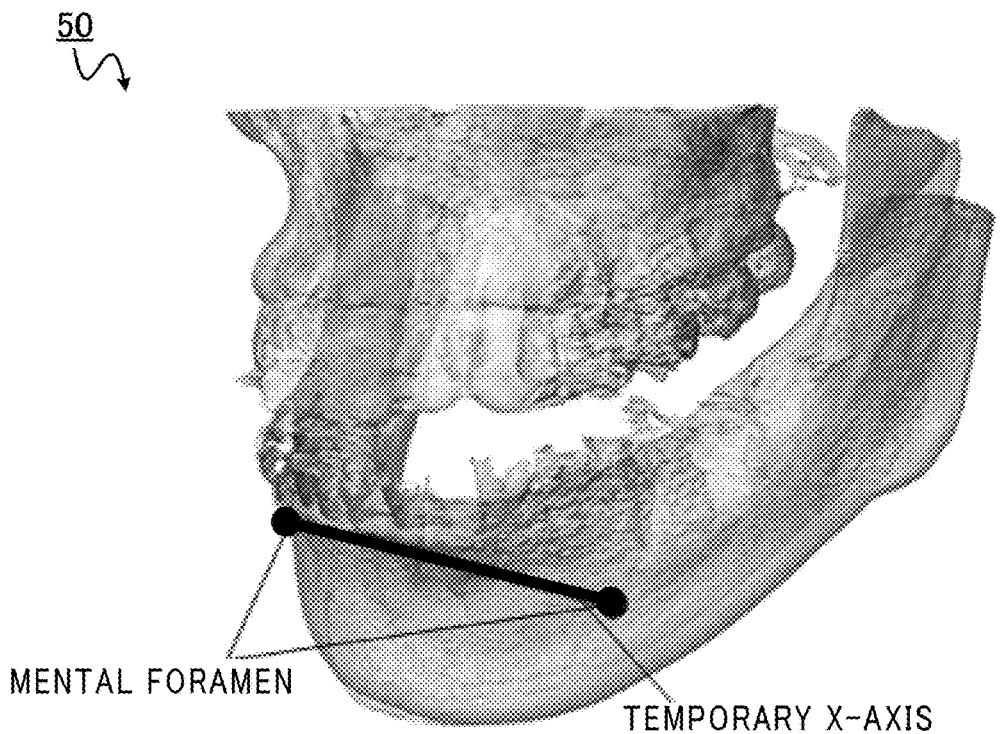
FIG. 3 shows an example in which a temporary X-axis of a world coordinate system is defined in the embodiment of the present disclosure.

First, the coordinate system setter 314 defines a vector from the position of the left mental foramen to the position of the right mental foramen as a temporary X-axis that is a temporary coordinate axis. The temporary X-axis is a temporary coordinate axis to set a world coordinate system. FIG. 3 shows the temporary X-axis defined in the three-dimensional image 50. As shown in FIG. 3, the temporary X-axis is represented as a straight line or a vector connecting the left and right mental foramina and laterally penetrating the lower jaw part.

Figure 4:
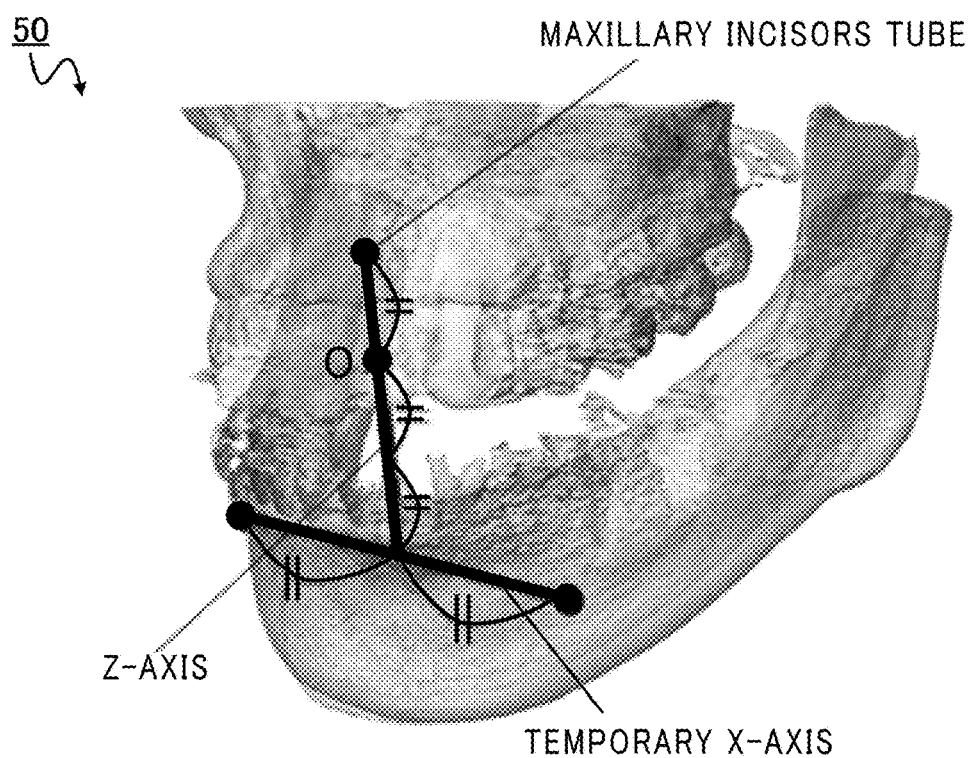
FIG. 4 shows an example in which a Z-axis and an origin of the world coordinate system are defined in the embodiment of the present disclosure.

Secondly, having finished defining the temporary X-axis, the coordinate system setter 314 defines a vector passing through the position of the maxillary incisors tube from a middle point of the position of the left mental foramen and the position of the right mental foramen as a Z-axis that is a first coordinate axis. Further, the coordinate system setter 314 defines, as an origin O, a position that internally divides, by a specified ratio, in particular, by a ratio of two thirds, a distance from the middle point of the left and right mental foramina to the position of the maxillary incisors tube. FIG. 4 shows the Z-axis and the origin O defined in the three-dimensional image 50. As shown in FIG. 4, the Z-axis is represented as a straight line or a vector extending from the lower jaw part to the upper jaw part. The origin O is set at a position closer to the upper jaw part between the lower jaw part and the upper jaw part.

Figure 5:
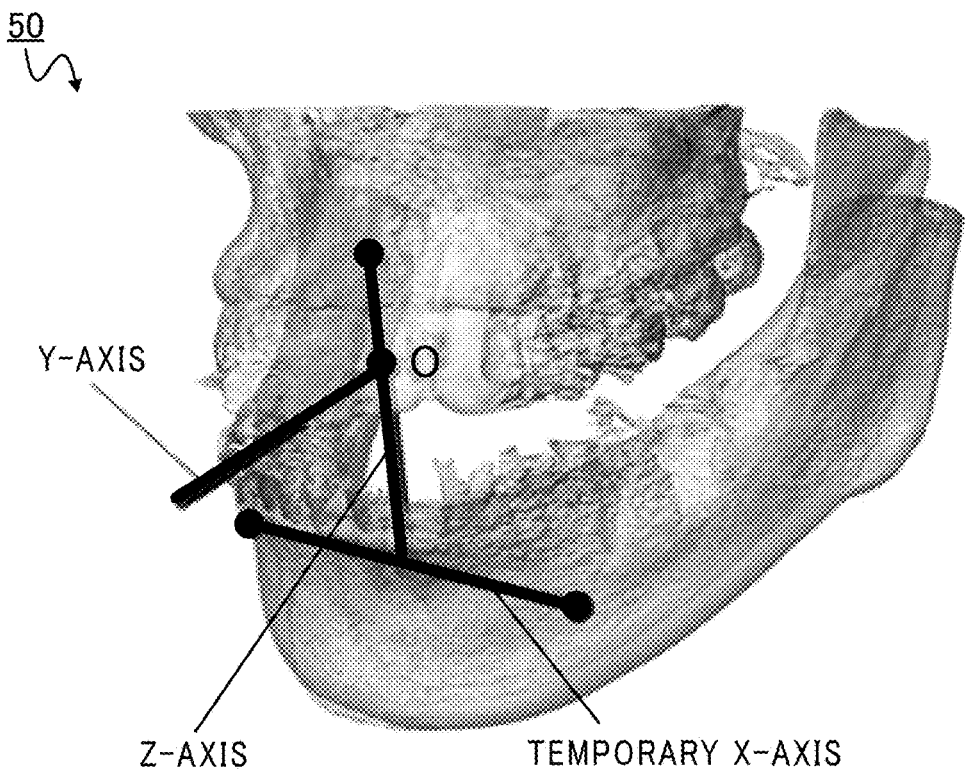
FIG. 5 shows an example in which a Y-axis of the world coordinate system is defined in the embodiment of the present disclosure.

Thirdly, having finished defining the Z-axis and the origin O, the coordinate system setter 314 defines a Y-axis as a second coordinate axis by using a cross product of the Z-axis and the temporary X-axis. In particular, the coordinate system setter 314 calculates a cross product of a three-dimensional vector representing the Z-axis and a three-dimensional vector representing the temporary X-axis and defines, as a Y-axis, a coordinate axis determined by the three-dimensional vector thus obtained. FIG. 5 shows the Y-axis defined in the three-dimensional image 50. As shown in FIG. 5, the Y-axis is defined as a coordinate axis that passes through the origin O and is perpendicular to the Z-axis and the temporary X-axis.

Figure 6:
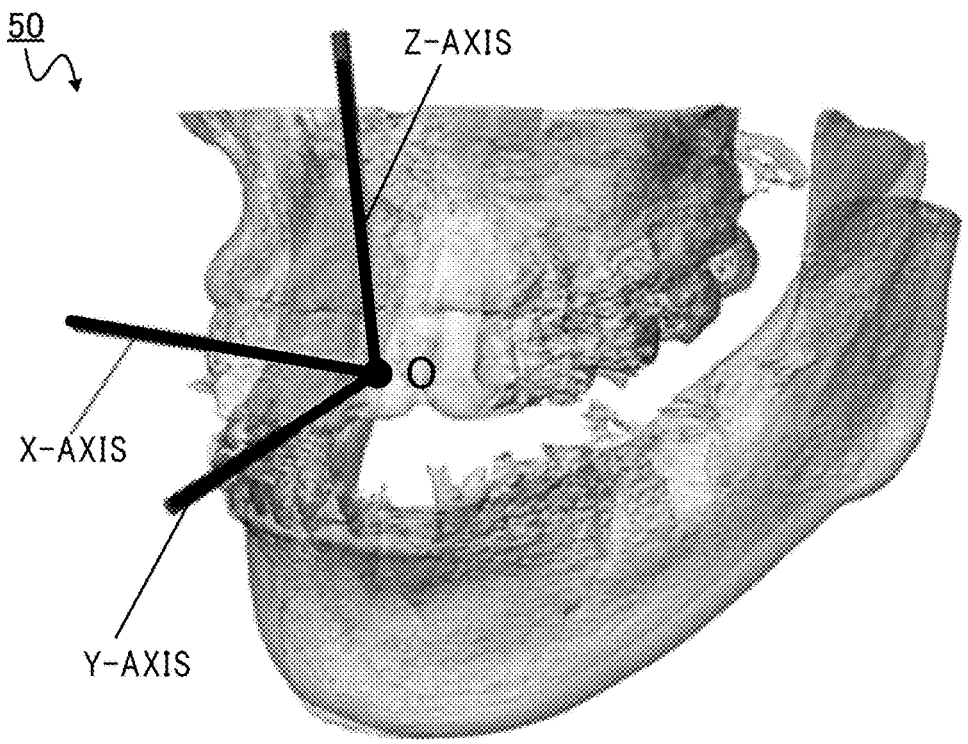
FIG. 6 shows an example in which an X-axis of the world coordinate system is defined in the embodiment of the present disclosure.

Fourthly, having finished defining the Y-axis, the coordinate system setter 314 defines an X-axis as a third coordinate axis by using a cross product of the Y-axis and the Z-axis. In particular, the coordinate system setter 314 calculates a cross product of a three-dimensional vector representing the Y-axis and a three-dimensional vector representing the Z-axis and defines, as an X-axis, a coordinate axis determined by the three-dimensional vector thus obtained. FIG. 6 shows the X-axis defined in the three-dimensional image 50. As shown in FIG. 6, the X-axis is defined as a coordinate axis that passes through the origin O and is perpendicular to the Y-axis and the Z-axis.

Figure 7:
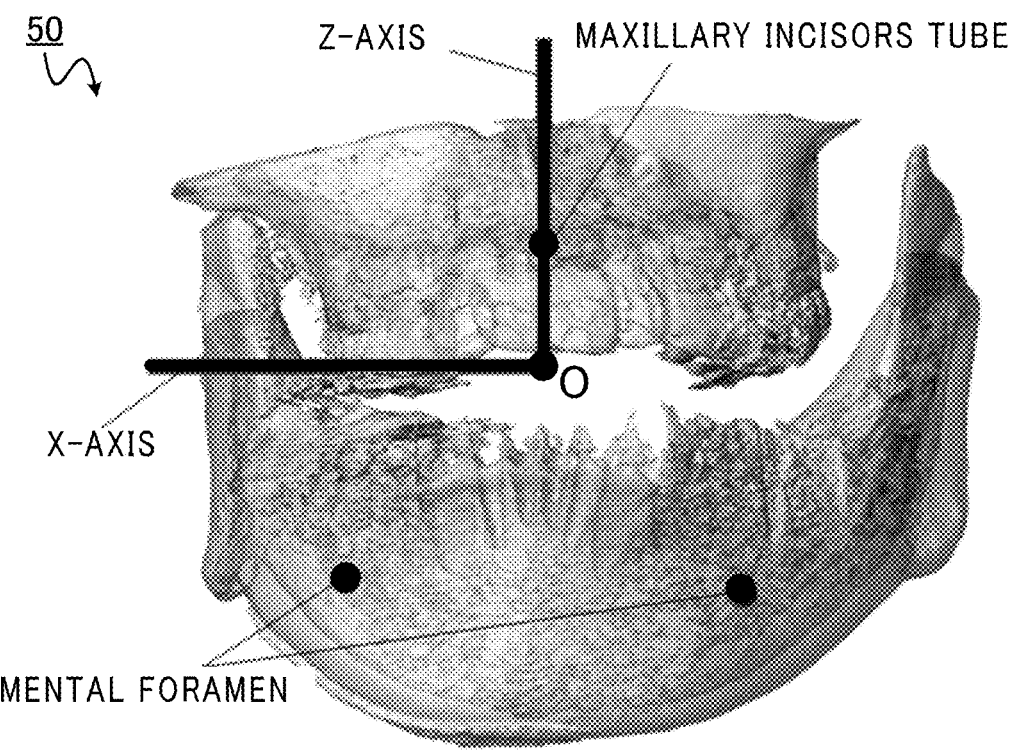
FIG. 7 shows a three-dimensional image in which the world coordinate system is set in the embodiment of the present disclosure as seen from the front of an upper jaw part and a lower jaw part.

In this way, the coordinate system setter 314 constructs, as a world coordinate system, a three-dimensional orthogonal coordinate system including the X-axis, the Y-axis and the Z-axis that are orthogonal to each other. FIG. 7 shows the world coordinate system thus constructed as viewed from the front of the upper jaw part and the lower jaw part, that is, along a line-of-sight parallel to the Y-axis (perpendicular to the X-Z plane). As shown in FIG. 7, the origin O of the world coordinate system is positioned at an approximate center of both cheeks, and a Y-Z plane is set as a median plane vertically passing through an approximate center of the upper jaw part, the lower jaw part and the oral cavity of the subject 10. Accordingly, the world coordinate system set by the coordinate system setter 314 is a coordinate axis suitable for evaluating an entirety of the teeth in the three-dimensional image 50. The coordinate system setter 314 works through coordination of the controller 310 with the storage 320. The coordinate system setter 314 functions as coordinate system setting means.

Referring to FIG. 2 again, the information acquirer 315 acquires information on a tooth of at least one of the upper jaw part or the lower jaw part represented by the world coordinate system set by the coordinate system setter 314. Information on a tooth refers to information indicating characteristics of the tooth such as a position, an orientation, and a state, which information is necessary for diagnosing or analyzing the tooth. The information acquirer 315 extracts information on a tooth from the three-dimensional image 50 by analyzing the three-dimensional image 50 where the world coordinate system is set. The information acquirer 315 works through coordination of the controller 310 with the storage 320. The information acquirer 315 functions as information acquisition means.

In particular, the information acquirer 315 acquires, as the information on the tooth, a dentition and a tooth axis of each of the upper jaw part and the lower jaw part. The dentition means an alignment of a plurality of teeth, that is, a tooth alignment. The information acquirer 315 acquires the dentition by calculating position coordinates of a plurality of teeth of the upper jaw part and the lower jaw part in the world coordinate system set by the coordinate system setter 314.

To be more specific, the information acquirer 315 acquires, as a position coordinate of each of a plurality of teeth constituting a dentition, a position coordinate of a center of gravity of each of the plurality of teeth. Here, the information acquirer 315 calculates a center of gravity of a three-dimensional shape that does not consider a pulp cavity, as disclosed for example in Non Patent Literature 3, in order to acquire a position coordinate of a center of gravity. Alternatively, the information acquirer 315 may calculate a center of gravity of each tooth while taking a pulp cavity into consideration. In this way, the information acquirer 315 acquires a dentition of each of the upper jaw part and the lower jaw part by calculating a position coordinate of each of the plurality of teeth.

The information acquirer 315 also acquires a tooth axis of each of a plurality of teeth of the upper jaw part and the lower jaw part. Here, the information acquirer 315 can use a technique disclosed in Non Patent Literature 3 as a technique to acquire a tooth axis. In particular, the information acquirer 315 calculates, by using the three-dimensional principle component analysis method, a three-dimensional vector as a longitudinal principle component, in the world coordinate system set by the coordinate system setter 314. The information acquirer 315 then acquires, as a tooth axis of each tooth, the three-dimensional vector thus calculated.

Having acquired a dentition and a tooth axis, the information acquirer 315 acquires an approximate curve that approximates position coordinates of a plurality of teeth constituting a dentition. The approximate curve is a curve that approximates a dentition in order to quantitatively evaluate and simply represent the same. The information acquirer 315 acquires, as an approximate curve, a curve obtained by regressing position coordinates of a plurality of teeth by using quadratic to fourth-order functions.

In particular, the information acquirer 315 projects the position coordinate of the center of gravity of each of the plurality of teeth obtained in the world coordinate system onto each of the X-Y plane and the X-Z plane in the world coordinate system. The information acquirer 315 then regresses the position coordinate of the center of gravity of each of the plurality of teeth thus projected, by using a quadratic function, a cubic function or a fourth-order function. In other words, the information acquirer 315 calculates a coefficient of a quadratic, cubic or fourth-order function that best approximates the coordinate values of the plurality of teeth thus projected. The information acquirer 315 acquires, as an approximate curve for approximating a dentition, a quadratic, a cubic or a fourth-order function curve that has the coefficient thus calculated.

Figure 8:
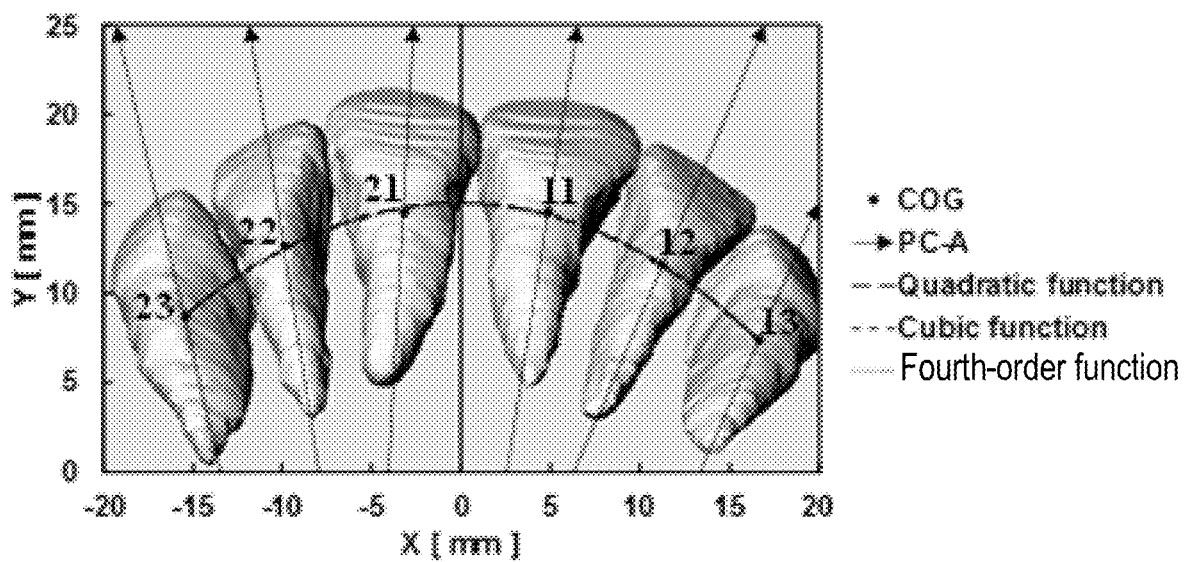
FIG. 8 shows a dentition of an upper jaw part of a subject projected onto an X-Y plane of the world coordinate system in the embodiment of the present disclosure together with a tooth axis and a regression curve.

FIG. 8 shows an example where a dentition of front teeth of the upper jaw part of the subject 10 (central incisor: FDI dental formula 11, 21; lateral incisor: FDI dental formula 12, 22; canine: FDI dental formula 13, 23) is projected onto the X-Y plane and represented together with a three-dimensional model of the front teeth and an approximate curve. FIG. 8 shows, as an approximate curve, a regression curve obtained by using a quadratic function, a cubic function and a fourth-order function. In FIG. 8, an orientation from a dental root to a tooth crown is defined as an orientation of a tooth axis, and the orientation is shown by an arrow. In this way, it is made easy to visually understand a relative positional and a relative orientation relationship of a plurality of teeth of the subject 10, by displaying the dentition, the tooth axis and the approximate curve acquired by the information acquirer 315, together with a three-dimensional dental model.

Note that the information acquirer 315 acquires an approximate curve not only when the dentition of the upper jaw part of the subject 10 is projected onto the X-Y plane as shown in FIG. 8, but also acquires an approximate curve by using the same technique when the dentition of the upper jaw part is projected onto the X-Z plane and when the dentition of the lower jaw part is projected onto the X-Y plane and the X-Z plane. Further, the information acquirer 315 can acquire an approximate curve by using the same technique when a dentition of any portion of the upper jaw part or the lower jaw part of the subject 10 is projected onto any plane.

Having thus acquired the approximate curve, the information acquirer 315 further calculates, as the information on the tooth, a difference between a position coordinate of each tooth and an approximate curve of a dentition. A tooth having a larger difference from an approximate curve means that the tooth needs to be straightened due to a larger deviation from the dentition. In particular, the information acquirer 315 calculates, as a difference between a position coordinate of each tooth projected onto the X-Y plane and the approximate curve, a distance from a position of the center of gravity of each tooth to the approximate curve in a Y-axis direction. The information acquirer 315 calculates, as a difference between a position coordinate of each tooth projected onto the X-Z plane and the approximate curve, a distance from the position of the center of gravity of each tooth to the approximate curve in a Z-axis direction. A magnitude of the difference or distance obtained works as an index showing to what degree a tooth is to be moved when the same is being straightened. An orientation of the difference obtained, that is, an orientation of deviation of each tooth from the approximate curve, works as an index showing in which direction a tooth is to be oriented. The magnitude and the orientation of the difference obtained works as indices for determining a planting position and a planting direction of a dental implant.

The outputter 316 outputs the information on a tooth acquired by the information acquirer 315. The information on a tooth acquired by the information acquirer 315 refers, in particular, to a position coordinate or a dentition and a tooth axis of each of a plurality of teeth, and an approximate curve that approximates the dentition obtained in the world coordinate system. The outputter 316 outputs information indicating such a dentition, a tooth axis and an approximate curve, by displaying the information on the display 340.

In one example, as shown in FIG. 8, the outputter 316 causes the display 340 to display an image of a dentition of the upper jaw part of the subject 10 projected onto the X-Y plane. The outputter 316 causes the display 340 to display the image shown in FIG. 8, as well as an image of a tooth of any portion of the upper jaw part or the lower jaw part of the subject 10 as projected onto any plane, together with an approximate curve of a dentition and a tooth axis. In this way, the outputter 316 can output an image representing information on a tooth of various portions of the subject 10 from various angles. The outputter 316 works through coordination of the controller 310 with the display 340. The outputter 316 functions as output means.

Further, the outputter 316 outputs information indicating a difference between each piece of positional information on each of a plurality of teeth acquired by the information acquirer 315 and the approximate curve of a dentition acquired by the information acquirer 315. In particular, the outputter 316 outputs information indicating a magnitude and an orientation of a difference between a position coordinate of each tooth and the approximate curve of a dentition acquired by the information acquirer 315. For example, the outputter 316 displays the image shown in FIG. 8 on the display 340, with an arrow indicating the magnitude and the orientation of the difference from the approximate curve displayed at a position of each tooth. This allows the operator to easily check which tooth, what orientation, and to what extend the tooth is to be moved when the same is being straightened.

In the above process, the outputter 316 may display, at a position distant, in a direction of a difference from the approximate curve, by a magnitude of the difference, from each of the position coordinate of each of a plurality of teeth acquired by the information acquirer 315 in the world coordinate system set by the coordinate system setter 314, an image representing each of the plurality of teeth. In particular, the outputter 316 may cause the display 340 to display, while being moved in a direction of a difference from the approximate curve, by a magnitude of the difference, a three-dimensional model of each tooth shown in FIG. 8, as an image representing each of the plurality of teeth. A three-dimensional model of each tooth is thus displayed at a position along an approximate curve of a dentition, which allows the operator to check, prior to actual straightening of teeth, an appearance of a straightened dentition.

A flow of processing executed by the imaging system 100 configured as above will be described referring to FIG. 9 and FIG. 10.

Figure 9:
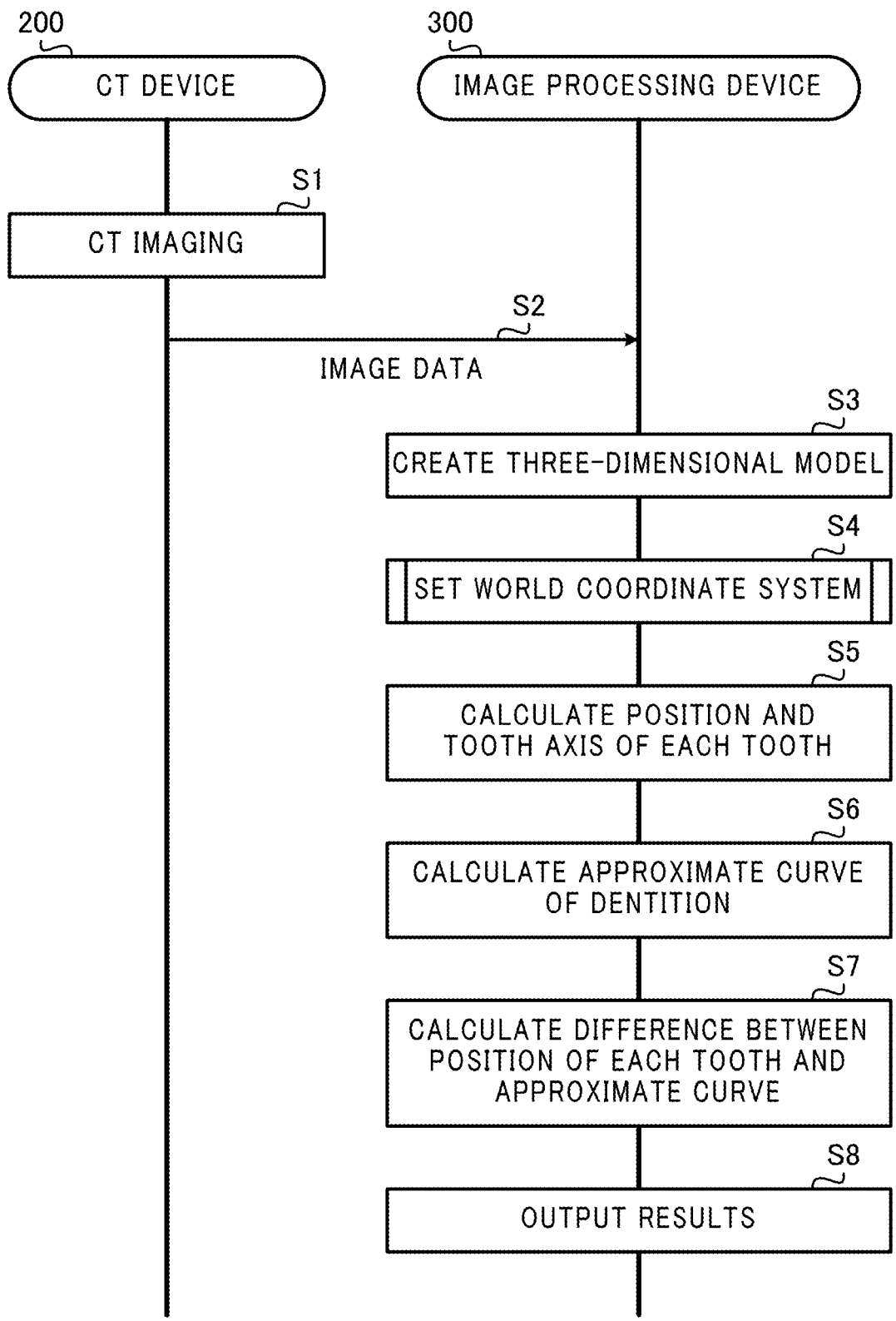
FIG. 9 is a sequence diagram showing a flow of processing executed in the imaging system according to the embodiment of the present disclosure.

FIG. 9 shows a flow of processing executed between the CT device 200 and the image processing device 300. The processing shown in FIG. 9 starts when the operator manipulates the CT device 200 to input an instruction to start CT imaging of the subject 10.

Having started the processing shown in FIG. 9, the control device 240 in the CT device 200 performs CT imaging of the subject 10 (step S1). In particular, the control device 240 irradiates an X-ray onto an imaging region including the upper jaw part and the lower jaw part of the subject 10 by using the X-ray generator 210 while rotating the arm 230, and detects the irradiated X-ray with the X-ray camera 220. This allows the control device 240 to acquire a plurality of CT images of an imaging region including the upper jaw part and lower jaw part of the subject 10 captured from various angles.

Having performed CT imaging, the CT device 200 transmits, to the image processing device 300, in response to a request by the image processing device 300 or voluntarily, image data showing a plurality of CT images obtained by CT imaging (step S2). The controller 310 in the image processing device 300 functions as the image data acquirer 311 and receives the image data transmitted from the CT device 200.

Having received the image data, the controller 310 functions as the reconfigurator 312 and creates a three-dimensional model from the received image data (step S3). In particular, the controller 310 reconfigures the three-dimensional image 50 from the plurality of CT images shown via the received image data. Accordingly, the controller 310 creates a three-dimensional model representing the upper jaw part and the lower jaw part of the subject 10.

Having created the three-dimensional model, the controller 310 sets a world coordinate system in the three-dimensional image 50 showing the three-dimensional model thus created (step S4). Processing to set the world coordinate system in step S4 will be detailed referring to the flowchart shown in FIG. 10.

Figure 10:
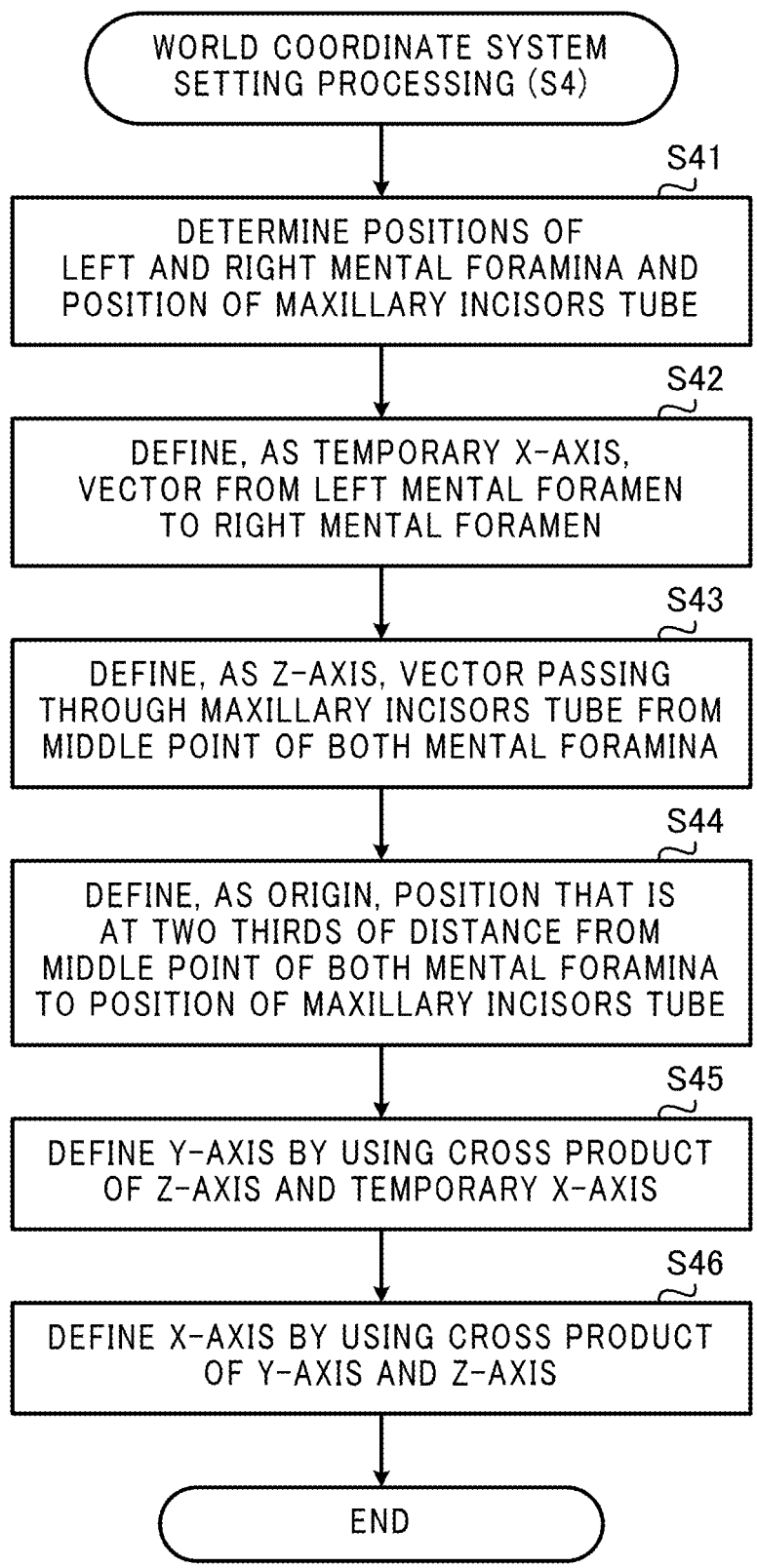
FIG. 10 is a flowchart showing a flow of processing to set the world coordinate system as executed by the image processing device according to the embodiment of the present disclosure.

Having started the processing to set a world coordinate system shown in FIG. 10, the controller 310 functions as the position determiner 313 and determines the positions of the left and right mental foramina and the position of the maxillary incisors tube (step S41). In particular, the operator manually identifies the positions of the left and right mental foramina and the position of the maxillary incisors tube of the subject 10 while watching the three-dimensional image 50 displayed on the display 340. The controller 310 accepts, from the operator via the operator 330, the positions thus identified by the operator, and determines the accepted positions as the positions of the left and right mental foramina and the position of the maxillary incisors tube.

Having determined the positions of the left and right mental foramina and the position of the maxillary incisors tube, the controller 310 defines, as a temporary X-axis, a vector from the left mental foramen to the right mental foramen (step S42). In particular, as shown in FIG. 3, the controller 310 defines, as the temporary X-axis in the world coordinate system, a vector connecting both mental foramina of the lower jaw part of the subject 10 with each other.

Having defined the temporary X-axis, the controller 310 defines, as a Z-axis, a vector passing through the maxillary incisors tube from a middle point of both mental foramina (step S43). The controller 310 then defines, as an origin O, a position that is at two thirds of a distance from the middle point of both mental foramina to the position of the maxillary incisors tube (step S44). In particular, as shown in FIG. 4, the controller 310 defines, as a Z-axis, a vector from a point on the temporary X-axis defined in the lower jaw part to the incisors tube of the upper jaw part, and defines, as an origin O, a position that internally divides, by a ratio of two thirds as a specified ratio, a distance therebetween.

Having defined the origin O, the controller 310 defines a Y-axis by using a cross product of the Z-axis and the temporary X-axis (step S45). In particular, the controller 310 calculates a cross product of the vector defined as the Z-axis and the vector defined as the temporary X-axis, and defines the obtained vector as a Y-axis. Consequently, as shown in FIG. 5, the Y-axis is defined as a coordinate axis that passes through the origin O and is perpendicular to the Z-axis and the temporary X-axis.

Having defined the Y-axis, the controller 310 defines an X-axis by using a cross product of the Y-axis and the Z-axis (step S46). In particular, the controller 310 calculates a cross product of the vector defined as the Y-axis and the vector defined as the Z-axis, and defines the obtained vector as an X-axis. Consequently, as shown in FIG. 6, the X-axis is defined as a coordinate axis that passes through the origin O and is perpendicular to the Y-axis and the Z-axis.

In this way, the controller 310 sets a world coordinate system as a three-dimensional orthogonal coordinate system in the three-dimensional image 50, acquired by the CT device 200, showing the upper jaw part and the lower jaw part of the subject 10. In steps S42 to S46, the controller 310 functions as the coordinate system setter 314.

Referring to FIG. 9 again, having set the world coordinate system in step S4, the controller 310 calculates a position and a tooth axis of each tooth (step S5). In particular, the controller 310 calculates a position coordinate of a center of gravity in the world coordinate system set in step S4, for each of the plurality of teeth of the subject 10 in the three-dimensional image 50. Further, the controller 310 calculates, as a tooth axis, a longitudinal three-dimensional vector of each tooth by using the three-dimensional principle component analysis method.

Having calculated the position and the tooth axis of each tooth, the controller 310 calculates an approximate curve of a dentition (step S6). In particular, the controller 310 projects position coordinates of the center of gravity of the plurality of teeth acquired in step S5 onto each of the X-Y plane and the X-Z plane. The controller 310 then regresses the position coordinates of the plurality of teeth projected onto each of the X-Y plane and the X-Z plane by using a quadratic, cubic or fourth-order function, and acquires the resulting regression curve as an approximate curve of the dentition.

Having calculated the approximate curve of the dentition, the controller 310 calculates a difference between the position of each tooth and the approximate curve (step S7). In particular, the controller 310 calculates a deviation of the position coordinate of each tooth from the approximate curve in each of the X-Y plane and the X-Z plane. This allows the controller 310 to acquire indices of a distance and an orientation of movement of the tooth when the same is being straightened. In steps S5 to S7, the controller 310 functions as the information acquirer 315.

Next, the controller 310 functions as the outputter 316 and outputs results of steps S5 to S7 (Step S8). In particular, the controller 310 causes the display 340 to display an image of a dentition, a tooth axis and an approximate curve of the dentition, such as the image shown in FIG. 8. Here, the controller 310 causes the display 340 to further display, on top of the image shown in FIG. 8, as indices of a distance and an orientation of movement of the tooth when the same is being straightened, an arrow or other information indicating a magnitude and an orientation of a difference between the position of each tooth and the approximate curve calculated in step S7.

In this way, the controller 310 sets the world coordinate system as a coordinate system encompassing an entirety of the three-dimensional image 50, and then acquires and displays information on a dentition, a tooth axis, and an approximate curve of the dentition as presented in the world coordinate system. This allows the operator to easily recognize a relative relationship between a plurality of teeth of the subject 10.

(Result of Experiment)

Next, a result of an experiment will be described that is performed to evaluate the world coordinate system and the approximate curve of the dentition obtained by the aforementioned imaging system 100.

In this experiment, all the teeth of six adults (four males, two females, average age 29) as subjects were imaged by using the CT device 200 of the cone beam system (KR-X SCAN from KINKI ROENTGEN INDUSTRIAL). In CT imaging, when upper and lower teeth are overlapped while being engaged with each other, it is difficult to evaluate a position and an orientation of each tooth, so that CT imaging was performed while the subject 10 was biting a plastic bite piece with a thickness of a tooth engaging portion of 2 mm. A three-dimensional image was reconfigured by using three-dimensional medical imaging construction software (Zed-View 9.3, LEXI) from a CT image acquired via CT imaging (tube voltage: 85 kV; tube current: 8 mA; voxel size: 0.256×0.256×0.256 mm; field of view: Φ23×123 mm), and a three-dimensional model of a tooth and a maxilla/mandible was created.

By using the three-dimensional model thus created, a tooth axis (principal component analysis-axis (PC-A)) and a center of gravity (COG) were calculated, of maxillary and mandibular central incisors (FDI dental formula 11, 21, 31, 41), lateral incisors (FDI dental formula 12, 22, 32, 42) and canines (FDI dental formula 13, 23, 33, 43). In particular, as disclosed in Non Patent Literature 3, a three-dimensional vector as a longitudinal principal component was obtained as a tooth axis PC-A by using the three-dimensional principle component analysis method, and a center of gravity of a three-dimensional shape not taking a pulp cavity into consideration was obtained as a center of gravity COG. Here, the tooth axis PC-A and the center of gravity COG were obtained in a local coordinate system individually set for each tooth.

Next, in order to evaluate an absolute spatial position of front teeth (central incisors, lateral incisors and canines), an origin O, an X-axis, a Y-axis and a Z-axis were defined to set a world coordinate system in accordance with the aforementioned procedure referring to FIG. 3 to FIG. 7 and FIG. 10, that is, from three characteristic points, that is, left and right mental foramina and a maxillary incisors tube. Then, the tooth axis PC-A and the center of gravity COG of the maxillary and mandibular central incisors, lateral incisors and canines as obtained in the local coordinate system were represented while being converted to vectors and coordinate values in the world coordinate system thus set.

In this experiment, a construction precision of a world coordinate system between different subjects was evaluated. In particular, a mean coordinate of the origins O of the world coordinate systems set for three subjects was obtained. Then, a three-dimensional distance from the mean coordinate thus obtained and each of the origins O for the three subjects was calculated as a spatial error of an origin O. As a result, the spatial error of the origin O was 0.45±0.20 mm in terms of a mean error and 0.94 mm in terms of a maximum error. The mean error of the origin O was 0.45±0.20 mm, which means that the construction precision of a world coordinate system between different subjects is within a clinically acceptable range.

A relative angular difference between the temporary X-axis and the X-axis defined when a world coordinate system was set for the three subjects was evaluated. As a result, a mean error between the temporary X-axis and the X-axis was 2.7±0.7° around the origin O in the X-Z plane. Accordingly, a repeatability of construction of a world coordinate system for any subject is sufficient. As described above, construction of a stable world coordinate system is based on an advantage that three characteristic points, that is, left and right mental foramina and a maxillary incisors tube, are clear as anatomical characteristic points of jawbone.

Figure 11:
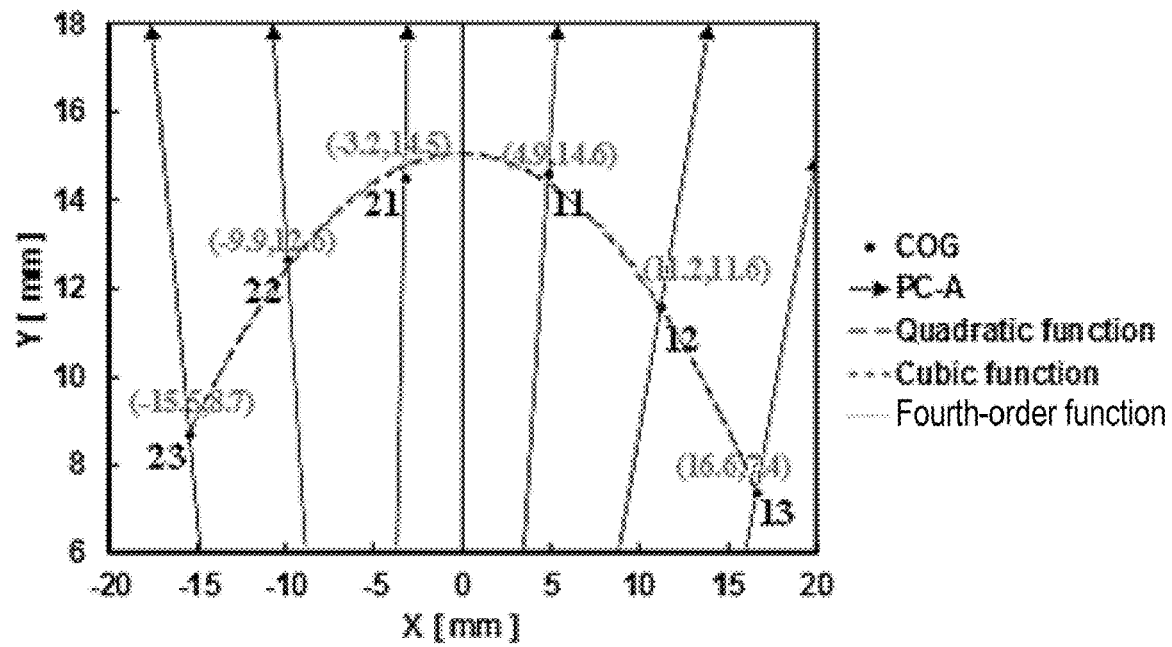
FIG. 11 shows a result of regression, by using quadratic to fourth-order functions, of the dentition of the upper jaw part of the subject as projected onto the X-Y plane of the world coordinate system in an evaluation experiment of the present disclosure.
Figure 12:
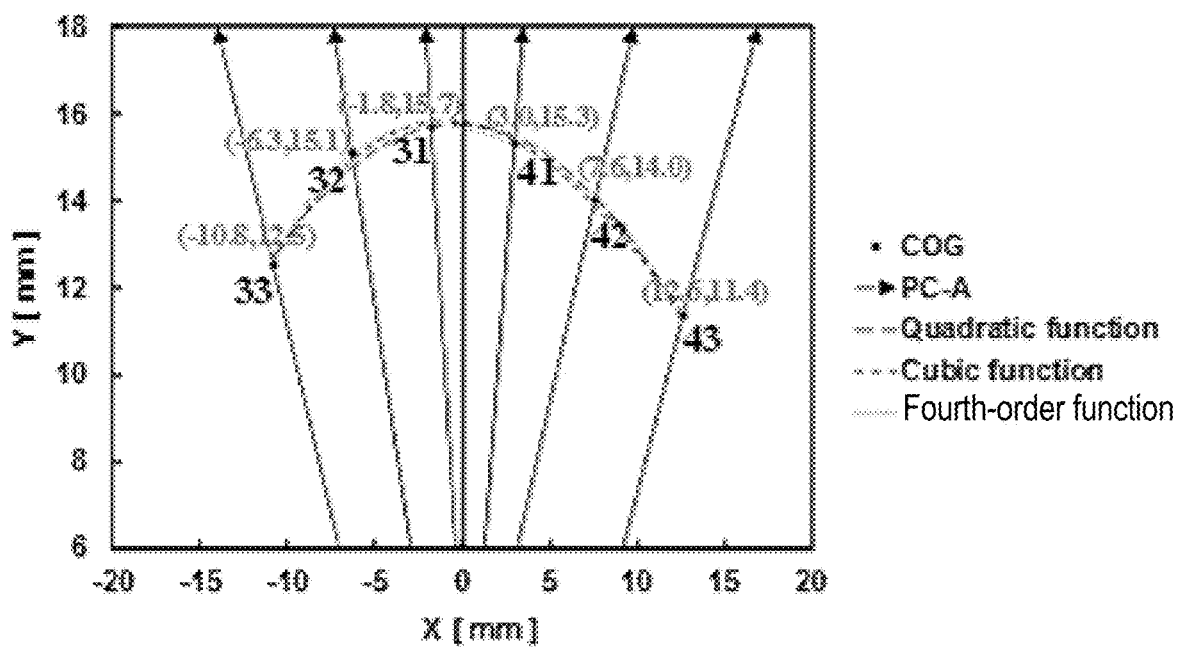
FIG. 12 shows a result of regression, by using quadratic to fourth-order functions, of the dentition of the lower jaw part of the subject as projected onto the X-Y plane of the world coordinate system in the evaluation experiment of the present disclosure.

Next, a result of regression, by using quadratic to fourth-order functions, of the dentition of each of the six subjects obtained in the world coordinate system, was evaluated. FIG. 11 and FIG. 12 show a result obtained, for one of the six subjects, by projecting a coordinate value of the center of gravity COG of each tooth acquired in the world coordinate system onto the X-Y plane in order to represent the dentition of the front teeth part of the upper jaw part and the lower jaw part, and regressing the projected coordinate value by using curves of quadratic to fourth-order functions. Further, FIG. 11 and FIG. 12 also show a straight line that appears when the tooth axis of each tooth is projected onto the X-Y plane.

In FIG. 11 and FIG. 12, curves obtained by regressing the coordinate value of the center of gravity COG of each tooth by using the quadratic, cubic and fourth-order functions appear almost overlapped one on the other. In particular, there is no significant difference between the quadratic regression curve and the cubic regression curve. On the other hand, the fourth-order regression curve is somewhat different from the quadratic or cubic regression curve. Almost the same result was obtained in a case where the dentitions of the upper jaw part and the lower jaw part were projected onto the Y-Z plane.

For each of the six subjects, regression of the dentition of the front teeth of the lower jaw part was performed by using quadratic to fourth-order functions to calculate a correlation coefficient r. As a result, the value of the correlation coefficient r was r=0.79-0.99 for the quadratic function, r=0.89-0.99 for the cubic function, and r=0.94-1.00 for the fourth-order function, which shows a tendency that the correlation coefficient r increases as the order of a regression curve increases. While it is evident that the correlation coefficient r rises by increasing the order of a regression curve, an increase in the order of a regression curve generates an inflection point. It is thus necessary to select a type of a regression curve in accordance with an objective. It is found, however, that use of a higher-order regression curve is less suitable for evaluating a dentition and a tooth axis as in this experiment, but showing the dentition and the tooth axis with a regression curve by using a low-order quadratic function is more suitable for the viewpoint of easy understanding and a reduced calculation amount. In other words, in the image processing device 300, it is suitable for the information acquirer 315 to acquire, as a regression curve that approximates a dentition, a curve obtained by regressing a dentition by using a quadratic function.

Figure 13:
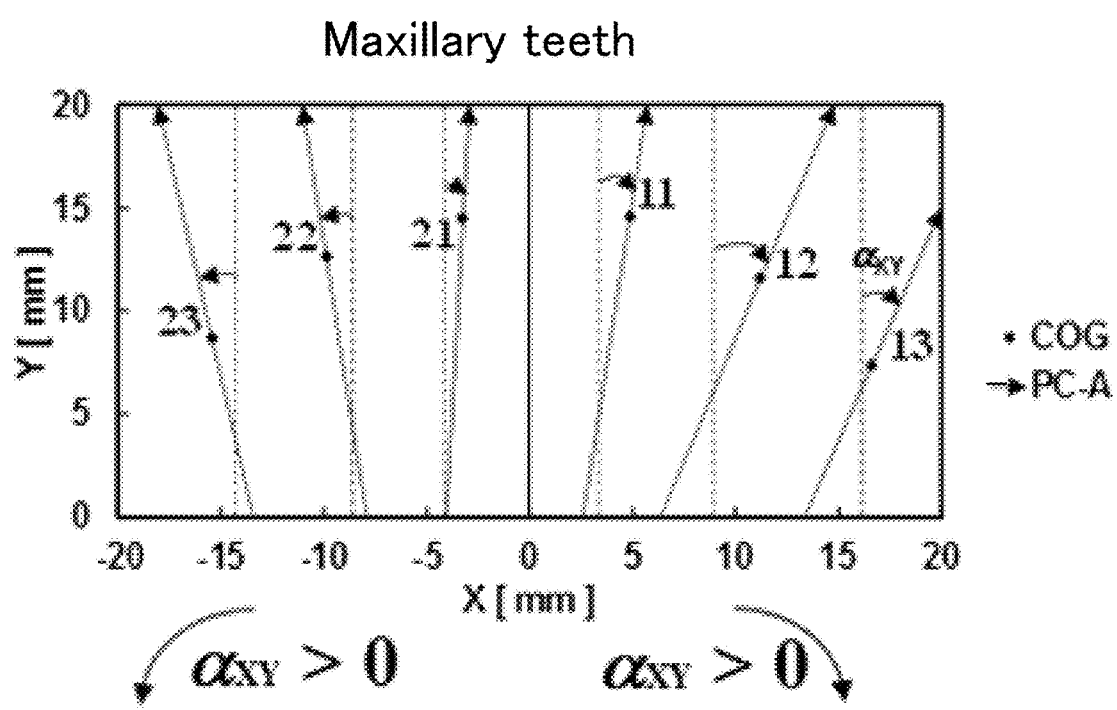
FIG. 13 shows the tooth axis of the upper jaw part of the subject as projected onto the X-Y plane of the world coordinate system in the evaluation experiment of the present disclosure.

Further, the tooth axis PC-A obtained in the world coordinate system for each of the six subjects was evaluated. FIG. 13 shows a tooth axis PC-A, projected onto the X-Y plane of the world coordinate system, of the front teeth (central incisors, lateral incisors and canines) of the upper jaw part of one subject. In FIG. 13, an angle formed by the tooth axis PC-A projected onto the X-Y plane and the Y-axis is defined as αXY. Here, an orientation of the angle αXY formed by the tooth axis PC-A of the upper/lower right front teeth and the Y-axis is defined as positive toward the right cheek with respect to the median plane (Y-Z plane) passing through the origin O, and the angle αXY formed by the tooth axis PC-A of the left front teeth and the Y-axis is defined as positive toward the left cheek with respect to the Y-Z plane. Note that the numerals 11 to 23 in FIG. 13 each represent an FDI dental formula. This is the same in FIG. 14.

Figure 14:
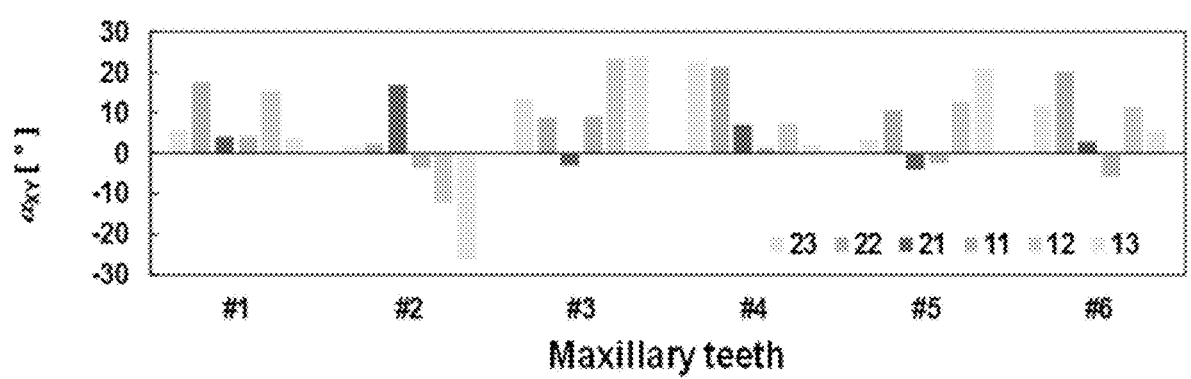
FIG. 14 shows, for each of six subjects, an angle formed by the tooth axis of the upper jaw part as projected onto the X-Y plane of the world coordinate system and the Y-axis in the evaluation experiment of the present disclosure.

FIG. 14 shows the angle αXY obtained for the front teeth (central incisors: 11, 21; lateral incisors: 12, 22; canines: 13, 23) of the upper jaw part of the six subjects (#1-#6). As shown in FIG. 14, the right front teeth (a central incisor: 11; a lateral incisor: 12; a canine: 13) are oriented toward the right cheek in most subjects and the left front teeth (a central incisor: 21; a lateral incisor: 22; a canine: 23) are generally oriented toward the left cheek. On the other hand, there is a case where right front teeth are oriented toward the left cheek as in the case of maxillary teeth (11, 12, 13) of the subject #2, which shows an individual difference. While not shown, evaluation is made in the same way as in FIG. 13 and FIG. 14 when the tooth axis PC-A of the lower jaw part is projected onto the X-Y plane or when the tooth axes PC-A of the upper and lower jaw parts are projected onto the X-Z plane.

As described above, the imaging system 100 and the image processing device 300 according to this embodiment set a world coordinate system based on the positions of the left and right mental foramina and the position of the maxillary incisors tube, in the three-dimensional image 50 showing the upper jaw part and the lower jaw part of the subject 10 acquired by CT imaging with the CT device 200. In this way, it is possible to uniquely define a world coordinate system that is universal and has a small individual difference as a coordinate system suitable for evaluating a relative relationship between a plurality of teeth of the subject 10, by setting a world coordinate system based on three characteristic points, that is, the left and right mental foramina and the maxillary incisors tube.

Further, the imaging system 100 and the image processing device 300 according to this embodiment calculates, as the information on the teeth of the subject 10, the dentition, the tooth axis and the approximate curve of the dentition in the world coordinate system and outputs the same. This makes it possible to evaluate characteristics, for example, a position and an orientation, of a tooth of the subject 10 through comparison of a plurality of teeth, and utilize the result of the evaluation in three-dimensional movement measurement of a tooth during dental straightening or in a preoperative plan for implant placement.

In particular, as a conventional technique to acquire a dentition, there is a technique to acquire a dentition by creating an intraoral model of the subject 10 and measuring the intraoral model by using a three-dimensional measuring machine or a digital caliper, or a technique to photograph an intraoral model into a photo image, followed by digitizing, or the like. These techniques, however, acquires a dentition from superficial characteristics of an upper tooth neck and thus has problems with accuracy and repeatability. On the other hand, the imaging system 100 and the image processing device 300 according to this embodiment sets, as a world coordinate system, a coordinate system that is universal and has a small individual difference by using characteristic points of the upper and lower jaw parts, and evaluates a relative relationship between a plurality of teeth of the subject 10 in the world coordinate system thus set. As a result, it is possible to more suitably evaluate characteristics defined by relative relationship between a plurality of teeth including a dentition, such as positions of a plurality of teeth with respect to a viscerocranium and a relative relationship between the positions of the plurality of teeth.

(Variant)

While an embodiment of the present disclosure has been described above, the present embodiment is an example and the scope of the present disclosure is not limited thereto. To put it differently, the above embodiment of the present disclosure is applicable in various ways and any embodiment is included in the scope of the present disclosure.

For example, in the above embodiment, the position determiner 313 determines the positions manually identified by the operator as the positions of the left and right mental foramina and the position of the maxillary incisors tube. In the present disclosure, however, the position determiner 313 may determine the positions of the left and right mental foramina and the position of the maxillary incisors tube by using a method other than manual identification by the operator. For example, the position determiner 313 may determine the positions of the left and right mental foramina and the position of the maxillary incisors tube by extracting characteristic points of the upper jaw part and the lower jaw part of the three-dimensional image 50 via a characteristic point extraction method.

In the above embodiment, the coordinate system setter 314 defines, as an origin O of a world coordinate system, a position that internally divides, by a ratio of two thirds, a distance from a middle point of the left and right mental foramina to the position of the maxillary incisors tube. In the present disclosure, however, the coordinate system setter 314 may define the origin O by using a different procedure from that of the above embodiment. For example, a specified ratio for defining the origin O is not limited to two thirds but may be another value. Alternatively, any position defined by the position of the left mental foramen, the position of the right mental foramen and the position of the incisors tube that are determined by the position determiner 313 may be used, without acquiring a middle point of the left and right mental foramina, to define the origin O. A procedure for defining first to third coordinate axes of the world coordinate system is not limited to the procedure for defining the X-axis, the Y-axis and the Z-axis, but may be any desired procedure.

In the above embodiment, the CT device 200 and the image processing device 300 are devices independent of each other. In the present disclosure, however, the CT device 200 and the image processing device 300 may be integrated with each other. In other words, a single device equipped with image capturing means for acquiring a three-dimensional image of the subject 10 may function as an imaging system according to the present disclosure. For example, the control device 240 in the CT device 200 may include a functionality of the aforementioned image processing device 300.

Alternatively, the image processing device 300 may be arranged, not only inside a medical facility where the CT device 200 is installed as in the above embodiment, but outside the medical facility and communicatively coupled with the CT device 200 via a wide area network. In this case, the image processing device 300 acquires CT image data from the CT device 200 via the wide area network and executes the aforementioned processing.

In the above embodiment, the CT device 200 is a device that acquires a CT image of the subject 10 via the cone beam system. In the present disclosure, however, the CT device 200 may acquire a CT image of the subject 10 via a different CT imaging system, that is, computer tomogram imaging. Additionally, a three-dimensional image of the subject 10 processed by the image processing device 300 is not limited to one acquired via CT imaging. For example, the image processing device 300 can execute the aforementioned processing on a three-dimensional image of the subject 10 acquired via magnetic resonance imaging (MRI).

In the above embodiment, the image processing device 300 includes the display 340. In the present disclosure, however, the display 340 may be arranged outside the image processing device 300. In this case, the outputter 316 outputs information on a tooth such as a dentition, a tooth axis or the like acquired by the information acquirer 315, transmitting the information to the display 340 arranged outside the image processing device 300 and causing the display 340 to display the information.

In the above embodiment, the controller 310 of the image processing device 300 functions as each component shown in FIG. 2 when the CPU executes a program stored in the ROM. In the present disclosure, however, the controller 310 may use, instead of the CPU, dedicated hardware functioning as a component shown in FIG. 2, such as an application specific integrated circuit (ASIC), a field-programmable gate array (FPGA), or a variety of control circuits. In this case, an individual functionality of each component may be provided by an individual hardware component or all of the functionalities of the components may be provided by a single hardware component. Alternatively, some of the functionalities of the components may be provided by the dedicated hardware and others may be provided by software or firmware. Note that entities including the dedicated hardware and the CPU to execute functionalities may be collectively called a processor.

Note that it is possible to, not only provide an existing information processing device or the like as an image processing device or an imaging system including in advance a configuration for offering a functionality according to the present disclosure, but also cause, through application of a program, the existing information processing device or the like to function as an image processing device or an imaging system according to the present disclosure. In other words, it is possible to cause the existing information processing device or the like to function as an image processing device or an imaging system according to the present disclosure, through application of a program for offering each functional configuration by the image processing device 300 or the imaging system 100 illustrated in the above embodiment for execution by a CPU or the like that controls the existing information processing device or the like.

Any method may be used to apply such a program. The program can be applied while being stored on a computer-readable storage medium such as a flexible disk, a compact disk (CD) -ROM, a digital versatile disc (DVD) -ROM, or a memory card. Further, the program can be embedded on a carrier wave and applied via a communication medium such as the Internet. For example, the program may be distributed by being posted on a bulletin board system (BBS) of a communication network. Then, by starting the program and running the same under the control of an operating system (OS), in the same way as other application programs, the above processing may be executed.

The foregoing describes some example embodiments for explanatory purposes. Although the foregoing discussion has presented specific embodiments, persons skilled in the art will recognize that changes may be made in form and detail without departing from the broader spirit and scope of the invention. Accordingly, the specification and drawings are to be regarded in an illustrative rather than a restrictive sense. This detailed description, therefore, is not to be taken in a limiting sense, and the scope of the invention is defined only by the included claims, along with the full range of equivalents to which such claims are entitled.

This application claims the benefit of Japanese Patent Application No. 2017-204342, filed on Oct. 23, 2017, the entire disclosure of which is incorporated by reference herein.

REFERENCE SIGNS LIST

10 Subject
50 Three-dimensional image
100 Imaging system
200 CT device
210 X-ray generator
220 X-ray camera
230 Arm
240 Control device
300 Image processing device
310 Controller
311 Image data acquirer
312 Reconfigurator
313 Position determiner
314 Coordinate system setter
315 Information acquirer
316 Outputter
320 Storage
330 Operator
340 Display
350 Communicator

The invention claimed is:

1. A dental image processing device comprising:
a position determiner configured to determine, in a three-dimensional image showing an upper jaw part of a subject and a lower jaw part of the subject, a position of a left mental foramen of the lower jaw part, a position of a right mental foramen of the lower jaw part, and a position of an incisors tube of the upper jaw part; and
a coordinate system setter configured to set a three-dimensional coordinate system having an origin at a position established by the position of the left mental foramen, the position of the right mental foramen, and the position of the incisors tube that are determined by the position determiner, the three-dimensional coordinate system including: a first coordinate axis that passes through the origin and the position of the incisors tube; a second coordinate axis that is perpendicular to the first coordinate axis and a straight line connecting the position of the left mental foramen and the position of the right mental foramen; and a third coordinate axis that is perpendicular to the first coordinate axis and the second coordinate axis.

2. The dental image processing device according to claim 1, wherein the coordinate system setter defines, as the origin, a position that internally divides, by a specified ratio, a distance from a middle point of the position of the left mental foramen and the position of the right mental foramen determined by the position determiner, to the position of the incisors tube determined by the position determiner.

3. The dental image processing device according to claim 2, wherein
the coordinate system setter defines:
as a temporary coordinate axis, a vector from the position of the left mental foramen to the position of the right mental foramen;
as the first coordinate axis, a vector passing through the position of the incisors tube from the middle point;
the second coordinate axis by a cross product of the first coordinate axis and the temporary coordinate axis; and
the third coordinate axis by a cross product of the second coordinate axis and the first coordinate axis.

4. The dental image processing device according to claim 1, further comprising:
an information acquirer configured to acquire information on a tooth of at least one of the upper jaw part or the lower jaw part, the information being represented by the three-dimensional coordinate system set by the coordinate system setter; and
an outputter configured to output the information on the tooth acquired by the information acquirer.

5. The dental image processing device according to claim 4, wherein the information acquirer acquires, as the information on the tooth, position coordinates of a plurality of teeth of at least one of the upper jaw part or the lower jaw part.

6. The dental image processing device according to claim 5, wherein the information acquirer acquires a position coordinate of a center of gravity of each of the plurality of teeth.

7. The dental image processing device according to claim 5, wherein
the information acquirer acquires an approximate curve for approximating the position coordinates of the plurality of teeth, and
the outputter outputs the position coordinates of the plurality of teeth and the approximate curve acquired by the information acquirer.

8. The dental image processing device according to claim 7, wherein
the information acquirer acquires, as the approximate curve, a curve obtained by regressing the position coordinates of the plurality of teeth by using a quadratic function.

9. The dental image processing device according to claim 7, wherein
the outputter outputs information indicating a difference between each of the position coordinates of the plurality of teeth acquired by the information acquirer and the approximate curve acquired by the information acquirer.

10. The dental image processing device according to claim 9, wherein
the outputter displays an image representing each of the plurality of teeth at a position distant, by a magnitude of the difference in a direction of the difference, from each of the position coordinates of the plurality of teeth acquired by the information acquirer in the three-dimensional coordinate system set by the coordinate system setter.

11. The dental image processing device according to claim 4, wherein
the information acquirer may acquire, as the information on the tooth, a tooth axis of the tooth.

12. A dental imaging system comprising:
the dental image processing device according to claim 1; and
an imaging device configured to capture images of the upper jaw part and the lower jaw part of the subject, wherein
the position determiner determines, in the three-dimensional image obtained via capturing by the imaging device, the position of the left mental foramen, the position of the right mental foramen, and the position of the incisors tube.

13. A dental image processing method comprising:
  determining, in a three-dimensional image showing an upper jaw part of a subject and a lower jaw part of the subject, a position of a left mental foramen of the lower jaw part, a position of a right mental foramen of the lower jaw part, and a position of an incisors tube of the upper jaw part; and
  setting a three-dimensional coordinate system having an origin at a position established by the determined position of the left mental foramen, the determined position of the right mental foramen, and the determined position of the incisors tube, the three-dimensional coordinate system including: a first coordinate axis that passes through the origin and the position of the incisors tube; a second coordinate axis that is perpendicular to the first coordinate axis and a straight line connecting the position of the left mental foramen and the position of the right mental foramen; and a third coordinate axis that is perpendicular to the first coordinate axis and the second coordinate axis.

14. A non-transitory computer readable recording medium storing a program for causing a computer to function as:
  a position determiner for determining, in a three-dimensional image showing an upper jaw part of a subject and a lower jaw part of the subject, a position of a left mental foramen of the lower jaw part, a position of a right mental foramen of the lower jaw part, and a position of an incisors tube of the upper jaw part; and
  a coordinate system setter for setting a three-dimensional coordinate system having an origin at a position established by the position of the left mental foramen, the position of the right mental foramen, and the position of the incisors tube that are determined by the position determiner, the three-dimensional coordinate system including: a first coordinate axis that passes through the origin and the position of the incisors tube; a second coordinate axis that is perpendicular to the first coordinate axis and a straight line connecting the position of the left mental foramen and the position of the right mental foramen; and a third coordinate axis that is perpendicular to the first coordinate axis and the second coordinate axis.

* * * * *